United States Patent [19]

Chapura et al.

[11] Patent Number: 5,399,356

[45] Date of Patent: Mar. 21, 1995

[54] PROCESS FOR MAKING SOLID DOSE FORMS CONTAINING BISMUTH

[75] Inventors: Francis B. Chapura, Hamilton; Daniel L. Barone, Delhi; Michael G. Colacino, Maineville, all of Ohio

[73] Assignee: The Procter & Gamble Company, Cincinnati, Ohio

[21] Appl. No.: 217,403

[22] Filed: Mar. 24, 1994

[51] Int. Cl.$^6$ .............................................. A61K 7/20
[52] U.S. Cl. .................................... 424/451; 424/441; 424/464; 424/484; 424/653; 424/715; 424/717; 514/159; 514/819
[58] Field of Search ............... 424/451, 464, 484, 715, 424/717, 653, 441; 427/2; 514/819, 159

[56] References Cited

U.S. PATENT DOCUMENTS

| | | | |
|---|---|---|---|
| 4,588,589 | 5/1986 | Sheth et al. | 514/159 |
| 4,741,855 | 5/1988 | Grote et al. | 252/142 |
| 4,744,987 | 5/1988 | Mehra et al. | 424/156 |
| 4,786,502 | 11/1988 | Chapura et al. | 424/441 |
| 4,940,695 | 7/1990 | Coveney et al. | 514/159 |
| 4,996,061 | 2/1991 | Webb et al. | 424/475 |
| 4,999,200 | 3/1991 | Casillan | 424/464 |
| 4,999,226 | 3/1991 | Schock et al. | 424/472 |
| 5,004,651 | 4/1991 | Becker | 424/465 |
| 5,045,321 | 9/1991 | Makino et al. | 424/475 |
| 5,093,132 | 9/1992 | Makino et al. | 424/475 |
| 5,096,714 | 3/1992 | Kuhrts | 424/439 |
| 5,169,640 | 12/1992 | France et al. | 424/470 |
| 5,192,752 | 3/1993 | Chapura et al. | 514/152 |
| 5,215,755 | 6/1993 | Roche et al. | 424/441 |
| 5,224,670 | 9/1993 | Upson et al. | 424/441 |
| 5,225,197 | 7/1993 | Bolt et al. | 424/440 |
| 5,225,202 | 7/1993 | Hodges et al. | 424/480 |
| 5,260,304 | 11/1993 | Gergely et al. | 424/464 |

FOREIGN PATENT DOCUMENTS

| | | | |
|---|---|---|---|
| 0547000 | 6/1993 | European Pat. Off. | A61K 31/19 |
| WO92/03126 | 3/1992 | WIPO | A61K 9/20 |
| 92/08463 | 5/1992 | WIPO | A61K 31/545 |
| WO93/09784 | 5/1993 | WIPO | A61K 31/60 |

OTHER PUBLICATIONS

Literature from FMC containing information, including particle size, regarding Avicel PH102.
Literature from FMC with general information regarding disintegrants.
Literature from Mendall containing Explotab product information.
USP lists for approved tablet disintegrants and wetting agents.
Test Product, Oct. 1991.
Pepto Formula Card.
08/217,524 Chapura, et al. Mar. 24, 1994.
08/144,592 Brideau, Carella Oct. 28, 1993.
08/030,754 Carella, Opiola Mar. 12, 1993.

*Primary Examiner*—Thurman K. Page
*Assistant Examiner*—Amy Hulina
*Attorney, Agent, or Firm*—Kathleen M. Harleston; Mary Catherine Poland; Douglas C. Mohl

[57] ABSTRACT

A process for making a bismuth-containing solid dose form composition is described which includes an agglomeration step with binder in a high shear mixer.

14 Claims, No Drawings

PROCESS FOR MAKING SOLID DOSE FORMS CONTAINING BISMUTH

BACKGROUND OF THE INVENTION

Pink Pepto-bismol ® liquid, which has bismuth subsalicylate as its active ingredient, is popular among consumers for quick relief of heartburn, indigestion, upset stomach, diarrhea, and nausea. Some consumers, though, do not like the taste or feel of such a liquid in their mouths, nor do they wish to chew a tablet with a similar taste. A swallowable tablet would be ideal for those consumers, but it is technically difficult to formulate and make a swallowable, bismuth-containing tablet which will give quick relief. To be valued by consumers, such a tablet must break up quickly in the stomach so that the active ingredient is absorbed into the blood rapidly enough to provide quick relief. An especially preferred, swallowable, bismuth-containing solid dose form provides relief from symptoms in about the same amount of time as liquid Pepto-bismol ® takes to provide relief.

U.S. Pat. No. 5,225,197, Bolt et al, issued Jul. 6, 1993, describes a chewable tablet which includes a medicament in a chewable base such as mannitol and an effervescent couple such as citric acid-sodium bicarbonate.

U.S. Pat. No. 5,096,714, Kuhrts, issued Mar. 17, 1992 describes a prolonged dosage composition consisting essentially of a gel-forming dietary fiber, a biologically absorbable drug or other therapeutic agent, and certain disintegrants, namely, a physiologically acceptable edible acid and a mineral salt which release a physiologically acceptable gas upon ingestion.

SUMMARY OF THE INVENTION

The present invention relates to a process for making a bismuth-containing solid dose form composition, comprising the steps of:

(a) mixing together in a mixer under high shear ingredients comprising: carbonate or bicarbonate salt; disintegrating agent; bismuth subsalicylate; and anionic surfactant or nonionic surfactant;

(b) agglomerating by mixing the product of (a) in a mixer under high shear with binder;

(c) drying the product of (b) to less than about 10% moisture, by weight of the composition; and (d) forming the product of (c) into a solid dose form, which comprises, by weight of the composition:

(1) from about 2% to about 25% of carbonate or bicarbonate salt;
(2) from about 0.5% to about 15% of disintegrating agent;
(3) from about 5% to about 70% of bismuth subsalicylate; and
(4) from about 0.1% to about 3% of anionic or nonionic surfactant.

DESCRIPTION OF THE INVENTION

I. The Process Steps

Step (a): Mixing

Step (a) is mixing together in a mixer under high shear ingredients comprising: carbonate or bicarbonate salt; disintegrating agent; bismuth subsalicylate; and anionic surfactant or nonionic surfactant. Steps (a) through (c) are preferably done in the same high shear mixer with drying capability.

Preferably, step (a1): drying the product of (a) into a fine powder, follows step (a) and precedes step (b). By "fine powder" is meant particles with an average particle size of between about 5 and about 300 microns. Preferred drying temperatures are listed below under step (c).

The bismuth subsalicylate is preferably in wet cake form. For this wet cake form, step (a1) drying is especially preferred to eliminate the excess water brought in by the wet cake. Without meaning to be bound by theory, it is believed that speed to relief of compositions made by this process is enhanced by the inclusion of the sodium starch glycolate and/or microcrystalline cellulose and/or calcium carbonate during step (a). Where wet cake is used, it is believed that the average particle size of the bismuth subsalicylate is kept small by the addition of these ingredients in this early step (a). Preferred average particle sizes are described below under "bismuth subsalicylate".

The ingredients in step (a) are preferably added to the high shear mixer in the following order of addition: carbonate or bicarbonate salt; disintegrating agent; bismuth subsalicylate; and anionic or nonionic surfactant.

Step (b): Agglomerating

Step (b) is agglomerating by mixing the product of (a) in a mixer under high shear with binder. In step (b), one or more additional dry ingredients is preferably added and the binder is sprayed onto the ingredients in the mixer.

The binder of step (b) is preferably selected from the group consisting of polyvinyl pyrrolidone, nonionic surfactant, anionic surfactant, water, and mixtures thereof. The binder of step (b) more preferably comprises water and polyvinyl pyrrolidone which is premixed and then sprayed on to the ingredients in the high shear mixer during mixing. The binder can be one of the other ingredients, such as surfactant, so long as it has binding capacity. Most preferred is water.

The binder of step (b) more preferably comprises water and polyvinyl pyrrolidone which is premixed and then sprayed on to the ingredients in the high shear mixer during mixing. Most preferably, the water is sprayed on to the ingredients in the mixer during mixing at a level of less than about 15% by weight of the composition.

The agglomerates preferably have an average particle size of between about 10 and about 1000 microns, preferably between about 50 and about 500 microns.

Step (c): Drying

Step (c) is drying the product of (b) to less than about 10%, preferably less than about 5%, most preferably less than about 3%, moisture, by weight of the composition.

Drying for this step or step (a1) is preferably at a temperature of between about 60° C. (15.5° F.) and about 150° C. (65.5° F.), more preferably between about 70° C. (21.1° F.) and about 120° C. (48.9° F.), most preferably between about 80° C. (26.6° F.) and about 100° C. (37.8° F.).

Preferably, a lubricant, such as magnesium stearate, is added after drying. Preferably, a glidant, such as silica, is also added after drying.

Step (d): Forming

Step (d) is forming the product of (c) into a solid dose form, which comprises, by weight of the composition:

(1) from about 2% to about 25% of carbonate or bicarbonate salt;
(2) from about 0.5% to about 15% of disintegrating agent;

(3) from about 5% to about 70% of bismuth subsalicylate; and (4) from about 0.1% to about 3% of anionic or nonionic surfactant.

These and additional preferred ingredients are described below.

Preferably, from about 15% to about 50% of microcrystalline cellulose is also included. Preferably, part of this microcrystalline cellulose is added in step (a).

The ingredients in step (d) preferably further comprise, by weight of the composition:

(a) from about 5% to about 20% of mannitol;

(b) from about 0.05% to about 0.2% of silica;

(c) from about 0.1% to about 5% of magnesium stearate; and (d) from about 1% to about 5% of polyvinyl pyrrolidone.

The solid dose form in step (d) is preferably a swallowable tablet or capsule, or a chewable tablet shaped like a capsule. Preferably, a rotary tablet press is used to form the tablet.

II. The Composition Ingredients

The solid dose form compositions herein are comprised of (bi)carbonate salt, disintegrating agent, bismuth subsalicylate, anionic or nonionic surfactant, and optionally microcrystalline cellulose, which are each described below. The present compositions preferably further comprise mannitol, silica, polyvinyl pyrrolidone, and other ingredients, which are also described below. The percentages given below are by weight of the composition unless otherwise indicated.

The preferably swallowable (i.e. not chewable) solid dose form compositions herein preferably do not comprise a gel-forming dietary fiber such as psyllium, or an effervescent couple such as citric acid-sodium bicarbonate, or a physiologically acceptable edible acid and a mineral salt which release a physiologically acceptable gas upon ingestion. The present compositions are not prolonged dosage compositions; instead they are designed for quick dissolution in the stomach and absorption into the bloodstream. It is not necessary to include calcium chloride in the present compositions.

A. Carbonate or Bicarbonate Salt

The compositions herein comprise from about 2% to about 25%, preferably from about 5% to about 20%, most preferably from about 8% to about 15%, by weight of the composition, of carbonate and/or bicarbonate salt. Preferred are calcium, sodium, potassium, and/or magnesium salts of carbonate (most preferred) and/or bicarbonate. Most preferred is calcium carbonate. Without meaning to be bound by theory, it is believed that the calcium carbonate at this level is acting as a processing aid and is not included to impart effervescence to this solid dose form.

B. Disintegrating Agent

The compositions herein comprise from about 0.5% to about 30%, preferably from about 1% to about 20%, most preferably from about 2% to about 10%, by weight of the composition, of disintegrating agent.

The disintegrating agent is preferably selected from the group consisting of sodium starch glycolate, cross-linked polyvinyl pyrrolidone, croscarmellose sodium (a cross-linked cellulose), polyacrilin potassium (an ion exchange resin), alginic acid, starch, and mixtures thereof. The disintegrating agent is more preferably sodium starch glycolate or cross-linked polyvinyl pyrrolidone (available as Crospovidone), and is most preferably sodium starch glycolate (available as Explotab ® from Edward Mendell Co.)

C. Bismuth Subsalicylate

The compositions herein comprise from about 5% to about 70%, preferably from about 10% to about 60%, most preferably from about 30% to about 50%, by weight of the composition, of bismuth subsalicylate. The average particle size of the bismuth subsalicylate (before incorporation with the remaining ingredients into the final form) is preferably from about 1 to about 50, more preferably from about 2 to about 30, most preferably from about 3 to about 10, microns. Without meaning to be bound by theory, this small particle size is believed to contribute to the efficacy of the solid dose forms herein by facilitating dissolution of the solid dose form in the stomach and allowing quicker absorption into the blood. Relief of symptoms is thus experienced rapidly, most preferably in an amount of time comparable to liquid Pepto-bismol ®.

D. Anionic or Nonionic Surfactant

The compositions herein comprise from about 0.1% to about 3%, preferably from about 0.2 to about 1%, most preferably from about 0.4 to about 0.6%, by weight of the composition, of anionic and/or nonionic surfactant. Any anionic and nonionic surfactants, including synthetics, suitable for use in a solid dose form (e.g., water dispersible) may be used in the present compositions.

Nonionic surfactants for use herein include compounds produced by the condensation of alkylene oxide groups (hydrophilic in nature) with an organic hydrophobic compound, which may be aliphatic or alkyl aromatic in nature. The surfactant is preferably a nonionic surfactant and is preferably selected from the group consisting of polyethylene oxide condensates of alkyl phenols; products derived from the condensation of ethylene oxide with the product resulting form the reaction of propylene oxide and ethylene diamine products; the condensation product of aliphatic alcohols having from 8 to 18 carbon atoms with ethylene oxide; long chain tertiary amine oxides corresponding to the following general formula $$R_1R_2R_3N \rightarrow O$$

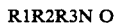

wherein R1 contains an alkyl, alkenyl, or monohydroxy alkyl radical of from about 8 to about 18 carbon atoms, from 0 to about 10 ethylene oxide moieties, and from 0 to 1 glyceryl moiety, and R2 and R3 contain from 1 to about 3 carbon atoms and from 0 to about 1 hydroxy group; long chain tertiary phosphine oxides; and long chain dialkyl sulfoxides containing one short chain alkyl or hydroxy alkyl radical of from 1 to about 3 carbon atoms and one long hydrophobic chain which contain alkyl, alkenyl, hydroxy alkyl, or keto alkyl radicals containing from about 8 to about 20 carbon atoms, from 0 to about 10 ethylene oxide moieties, and from 0 to 1 glyceryl moiety; and mixtures thereof.

The most preferred surfactant for use herein is polyoxyethylene sorbitan monooleate.

Anionic surfactants for use herein include the alkali metal salts of organic sulfuric reaction products having in their molecular structure an alkyl radical containing from 8–22 carbon atoms and a sulfonic acid or sulfuric acid ester radical.

If the surfactant is an anionic surfactant, it is preferably selected from the group consisting of: the sodium, ammonium, potassium or triethanolamine alkyl sulfates, sodium coconut oil fatty acid monoglyceride sulfates and sulfonates, sodium or potassium salts of sulfuric acid esters of the reaction product of 1 mole of a higher fatty alcohol and 1 to 12 moles of ethylene oxide, sodium or potassium salts of alkyl pheno ethylene oxide per molecule and in which the alkyl radicals contain from 8 to 12 carbon atoms, sodium alkyl glyceryl ether sulfonates, the reaction products of fatty acids having from 10 to 22 carbon atoms esterified with isethionic acid and neutralized with sodium hydroxide, water soluble salts of condensation products of fatty acids with sarcosine, and mixtures thereof.

E. Microcrystalline Cellulose

The compositions herein preferably further comprise from about 15% to about 50%, preferably from about 20% to about 40%, most preferably from about 25% to about 35%, by weight of the composition, of microcrystalline cellulose. Preferred is Avicel ® PH102 microcrystalline cellulose NF from FMC Corp. (Philadelphia, Pa.). Preferably, the average particle size of the microcrystalline cellulose is from about 20 to about 200 microns, most preferably from about 80 to about 120 microns.

F. Optional Ingredients

The compositions herein preferably further comprise, by weight of the composition:

(a) from about 2% to about 25%, preferably from about 5% to about 20%, most preferably from about 8% to about 15%, of soluble sugars and/or sugar alcohols, most preferably mannitol;

(b) from about 0.02% to about 0.5%, preferably from about 0.05% to about 0.2%, most preferably from about 0.08% to about 0.15%, of silica, most preferably Cab-o-Sil ® from Cabot Corp.;

(c) from about 0.1% to about 5%, preferably from about 0.5% to about 2%, most preferably from about 0.6% to about 1.5%, of magnesium stearate; and (d) from about 0.5% to about 10%, preferably from about 1% to about 5%, most preferably from about 1.5% to about 3%, of polyvinyl pyrrolidone, most preferably Povidone ®.

The soluble sugars are preferably selected from the group consisting of dextrose, sucrose, glucose, xylose, ribose, mannose, galactose, fructose, maltose, and mixtures thereof, and the sugar alcohols are preferably selected from the group consisting of xylitol, mannitol, sorbitol, and mixtures thereof. Most preferred is mannitol.

Conventional ingredients of swallowable, solid dose forms, such as dye, may also be included herein.

A preferred composition herein comprises, by weight of the composition:

(a) from about 8% to about 15% of calcium carbonate;

(b) from about 2% to about 10% of sodium starch glycolate;

(c) from about 3% to about 50% of bismuth subsalicylate;

(d) from about 0.4% to about 0.6% of anionic or nonionic surfactant; and (e) from about 25% to about 35% of microcrystalline cellulose.

It preferably further comprises, by weight of the composition:

(a) from about 5% to about 20% of mannitol;

(b) from about 0.05% to about 0.2% of silica;

(c) from about 0.1% to about 5% of magnesium stearate; and (d) from about 1% to about 5% of polyvinyl pyrrolidone.

G. Methods

The present invention further relates to a method for treating heartburn, indigestion, upset stomach, diarrhea, and/or nausea in humans or other mammals, the method comprising administering to a human or other mammal in need of such treatment a safe and effective amount of a pharmaceutical composition made by a process according to the present invention.

H. Form

The composition herein is preferably in the form of a tablet or capsule, more preferably in the form of a tablet shaped like a capsule. Conventional tablet/capsule making procedures are employed. Tablet hardness should be low enough to provide integrity and stability, but not so high as to interfere with dissolution of the tablet in the stomach.

The composition herein is preferably orally self-administered by humans and is preferably used for treating the same symptoms that liquid Pepto-bismol ® is used to treat. The tablets/capsules are preferably taken by mouth to relieve heartburn, indigestion, upset. stomach, diarrhea, and/or nausea in humans or other mammals. A composition herein is preferably orally administered for treatment of acid indigestion, heartburn or sour stomach.

Preferably, two caplets of about 675 milligrams per caplet (which includes approximately 262 milligrams of bismuth subsalicylate per caplet) are taken with water every ½ to 1 hour as needed up to a maximum of 8 doses in a 24 hour period (adult dose). The recommended dose for children 9–12 years of age is one caplet, for children 6–9 years of age is ⅔ caplet, for children 3–6 years of age is ⅓ caplet. Children under 3 should see a physician.

The following examples illustrate the compositions and processes of the present inventions. They are presented by way of example only and are not to be construed as limiting the scope of these inventions. It will appear to those of ordinary skill in the art upon reviewing the modifications described herein that various additional, related modifications may be made. Such modifications are intended to be within the scope of this invention.

All parts, percentages and ratios herein are by weight unless otherwise indicated. All references cited herein are expressly incorporated by reference.

EXAMPLE I

Swallowable Caplet

A swallowable caplet composition of the present invention is as follows.

| Ingredient | milligrams/caplet |
| --- | --- |
| Bismuth subsalicylate | 262.5 |
| Microcrystalline cellulose, NF[1] | 213.3 |
| Calcium carbonate | 67.5 |
| Mannitol | ⁻67.5 |
| Sodium starch glycolate[2] | 40.5 |
| Polyvinyl pyrrolidone[3] | 13.5 |
| Magnesium stearate, NF | 5.4 |
| Polysorbate 80[4] | 3.4 |
| Silica 5 | 0.7 |
| Dye | 0.7 |

| Ingredient | milligrams/caplet |
| --- | --- |
| Total | 675.0 |

[1] Available as Avicel ® PH102 from FMC Corp.
[2] Available as Explotab ® from Edward Mendell Co.
[3] Available as Povidone ®
[4] Available as Tween ® 80 from ICI
[5] Available as Cab-o-Sil ® from Cabot Corp.

Preferably, the ingredients are added to a mixer or granulator, preferably a Processall (made by Processall of Cincinnati, Ohio) or a Littleford (made by Littleford of Kentucky), in the following order: part of the microcrystalline cellulose, the calcium carbonate, part of the sodium starch glycolate, the Polysorbate 80, the dye, and the bismuth subsalicylate. After the addition of the bismuth subsalicylate and mixing at high shear, the mixture is dried at 86° C. (187° F.) in the Processall to less than 2% moisture. Additional powders (microcrystalline cellulose, sodium starch glycolate, mannitol and polyvinyl pyrrolidone) are added, and granules are formed by spraying water (approximately 10% by weight of the composition) onto the mixture under high shear in the Processall. After additional drying, still in the Processall, to less than 3% moisture, silica (glidant) and magnesium stearate (lubricant) are added and mixed for about one minute. Caplets are then formed on a rotary tablet press. Two caplets of about 675 milligrams per caplet are taken with water every ½ to 1 hour as needed up to a maximum of 8 doses in a 24 hour period (adult dose).

This composition can alternatively be compressed into tablet or capsule form. Alternative ingredients disclosed in this specification can be substituted for the above ingredients. The amounts of these ingredients can be varied within the ranges specified herein.

EXAMPLE II

Swallowable Tablet

A swallowable tablet composition of the present invention is as follows.

| Ingredient | milligrams/tablet |
| --- | --- |
| Bismuth subsalicylate | 262.5 |
| Microcrystalline cellulose | 186.5 |
| Calcium carbonate | 15.0 |
| Croscarmellose sodium | 10.0 |
| Polyvinyl pyrrolidone | 20.0 |
| Magnesium stearate | 5.0 |
| Polysorbate 80 | 1.0 |

Ingredients are mixed under high shear according to Example I. The disintegrating agent here is Croscarmellose sodium. Tablets are formed using a rotary tablet press.

What is claimed is:

1. A process for making a bismuth-containing solid dose form composition, comprising the steps of:
    (a) mixing together in a mixer under high shear ingredients comprising: carbonate or bicarbonate salt; disintegrating agent; bismuth subsalicylate; and anionic surfactant or nonionic surfactant;
    (b) agglomerating by mixing the product of (a) in a mixer under high shear with binder;
    (c) drying the product of (b) to less than about 10% moisture, by weight of the composition; and
    (d) forming the product of (c) into a solid dose form selected from the group consisting of a swallowable tablet, a swallowable capsule and a chewable tablet shaped like a capsule, which comprises, by weight of the composition:
        (1) from about 2% to about 25% of carbonate or bicarbonate salt;
        (2) from about 0.5% to about 15% of disintegrating agent;
        (3) from about 5% to about 70% of bismuth subsalicylate; and
        (4) from about 0.1% to about 3% of anionic or nonionic surfactant.

2. A process according to claim 1 wherein step (a1): drying the product of (a) into a fine powder having an average particle size of between about 5 and 300 microns, follows step (a) and precedes step (b).

3. A process according to claim 2 wherein the ingredients in step (a) are added to the high shear mixer in the following order of addition: carbonate or bicarbonate salt; disintegrating agent; bismuth subsalicylate; and anionic or nonionic surfactant.

4. A process according to claim 2 wherein the binder of step (b) is selected from the group consisting of polyvinyl pyrrolidone, nonionic surfactant, anionic surfactant, water, and mixtures thereof.

5. A process according to claim 4 wherein the ingredients in step (d) further comprise from about 15% to about 50% of microcrystalline cellulose, and wherein part of this microcrystalline cellulose is added in step (a).

6. A process according to claim 5 wherein in step (b), one or more additional dry ingredients is added and the binder is sprayed onto the ingredients in the mixer.

7. A process according to claim 6 wherein the binder of step (b) is water.

8. A process according to claim 5 wherein the binder of step (b) comprises water and polyvinyl pyrrolidone which is premixed and then sprayed on to the ingredients in the high shear mixer during mixing.

9. A process according to claim 6 wherein the binder of step (b) comprises water which is sprayed on to the ingredients in the mixer during mixing at a level of less than about 15% by weight of the composition.

10. A process according to claim 9 wherein step (c) drying is to a moisture level of less than about 3%, by weight of the composition.

11. A process according to claim 5 wherein the ingredients in step (d) further comprise, by weight of the composition:
    (a) from about 5% to about 20% of mannitol;
    (b) from about 0.05% to about 0.2% of silica;
    (c) from about 0.1% to about 5% of magnesium stearate; and
    (d) from about 1% to about 5% of polyvinyl pyrrolidone.

12. A process according to claim 10 wherein the disintegrating agent is selected from the group consisting of sodium starch glycolate, cross-linked polyvinyl pyrrolidone, croscarmellose sodium, polyacrilin potassium, alginic acid, starch, and mixtures thereof.

13. A process according to claim 12 wherein the surfactant is a nonionic surfactant.

14. A process according to claim 13 wherein step (c) drying is at at a temperature of between about 60° C. (15.5° F.) and about 150° C. (65.5° F.).

* * * * *